(12) United States Patent
Hunt et al.

(10) Patent No.: US 7,780,685 B2
(45) Date of Patent: Aug. 24, 2010

(54) ADHESIVE AND MECHANICAL FASTENER

(75) Inventors: John V. Hunt, Cincinnati, OH (US);
Daniel W. Price, Loveland, OH (US);
Mark S. Ortiz, Milford, OH (US);
Frederick E. Shelton, IV, Hillsboro,
OH (US); Christopher W. Widenhouse,
Clarksville, OH (US); Ronald J. Kolata,
Cincinnati, OH (US); James W. Voegele,
Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 380 days.

(21) Appl. No.: 11/558,002

(22) Filed: Nov. 9, 2006

(65) Prior Publication Data

US 2008/0114383 A1 May 15, 2008

(51) Int. Cl.
*A61B 17/08* (2006.01)

(52) U.S. Cl. .................. 606/151; 606/142; 606/143; 606/153; 606/213; 606/219; 606/220; 411/511

(58) Field of Classification Search .................. 606/75, 606/119–120, 142–143, 151–158, 213, 215, 606/219–220, 280, 289, 291; 227/8, 16, 227/19, 901–902; 24/114.6, 304; 604/415; 411/511–512, 520–530
See application file for complete search history.

(56) References Cited

U.S. PATENT DOCUMENTS

| | | | | |
|---|---|---|---|---|
| 4,060,089 A | * | 11/1977 | Noiles | 606/220 |
| 4,402,445 A | * | 9/1983 | Green | 227/19 |
| 4,589,416 A | * | 5/1986 | Green | 606/220 |
| 4,766,898 A | | 8/1988 | Hardy et al. | |
| 4,805,617 A | * | 2/1989 | Bedi et al. | 606/220 |
| 5,016,369 A | * | 5/1991 | Parry | 40/301 |
| 5,258,011 A | * | 11/1993 | Drews | 606/220 |
| 5,597,107 A | | 1/1997 | Knodel et al. | |
| 5,928,611 A | | 7/1999 | Leung | |
| 5,951,552 A | | 9/1999 | Long et al. | |
| 6,666,873 B1 | | 12/2003 | Cassell | |
| 6,692,507 B2 | * | 2/2004 | Pugsley et al. | 606/153 |
| 6,786,909 B1 | * | 9/2004 | Dransfeld et al. | 606/283 |
| 6,869,436 B2 | * | 3/2005 | Wendlandt | 606/151 |
| 6,926,722 B2 | * | 8/2005 | Geitz | 606/142 |
| 7,455,682 B2 | * | 11/2008 | Viola | 606/219 |
| 2002/0173848 A1 | * | 11/2002 | Sachs | 623/10 |
| 2003/0120265 A1 | * | 6/2003 | Deem et al. | 606/1 |
| 2003/0220660 A1 | * | 11/2003 | Kortenbach et al. | 606/151 |
| 2004/0059349 A1 | * | 3/2004 | Sixto et al. | 606/139 |
| 2004/0190975 A1 | | 9/2004 | Goodman et al. | |
| 2006/0085033 A1 | * | 4/2006 | Criscuolo et al. | 606/219 |
| 2006/0235469 A1 | * | 10/2006 | Viola | 606/219 |

* cited by examiner

*Primary Examiner*—(Jackie) Tan-Uyen T Ho
*Assistant Examiner*—Mark Mashack
(74) *Attorney, Agent, or Firm*—Frost Brown Todd LLC

(57) ABSTRACT

Provided is a two-piece anastomosis fastener that can be used to join two tissue sections together in accordance with Natural Orifice Transendoscopic Surgery (NOTES). The fastener may be releasably attached to a fastener applying instrument for delivery in accordance with such procedures. The fastener includes a first member and a second member, where the clamp members are operably configured to fasten together to clamp and hold tissue, such as gastric tissue, in juxtaposition to establish an anastomosis. The first clamp member and the second clamp member are coupled with an adhesive.

9 Claims, 7 Drawing Sheets

ADHESIVE AND MECHANICAL FASTENER

FIELD OF THE INVENTION

The present invention relates, in general, to surgical devices for the anastomosis of organs, and in particular to tissue fasteners, surgical devices for deploying tissue fasteners, and methods of use during surgery.

BACKGROUND OF THE INVENTION

Obese patients may experience increased morbidity from excess weight. The extra weight places a strain on body circulatory systems, respiratory systems, and the digestive system, and can stress or overload body organs causing numerous medical conditions such as diabetes, high blood pressure, high cholesterol, and sleep apnea. It can also increase the risk of a major coronary event. Bariatric medicine is focused on the prevention, control, and treatment of obesity. A change in diet, drugs, and surgery are the most common tools used to reduce a patient's caloric intake, reduce their weight, and save their lives.

Bariatric surgical techniques often result in dramatic weight loss for the morbidly obese. These surgeries may include stomach stapling to create a small pouch, intestinal bypass surgery, gastric banding, placement of a large filler object in the stomach to reduce the internal volume of the stomach, and gastric sleeves. The advent of laparoscopic surgery, also known as "keyhole" surgery, has revolutionized many surgical procedures. It has boosted demand for bariatric surgery, in particular, because it generally requires only a few small incisions resulting in a reduced recovery time.

Natural orifice transendoscopic surgery, herein referred to as NOTES, generally requires no incisions because instruments, such as staple guns, can be inserted through the mouth and snaked down the esophagus. If the work to be done involves the lower portion of the intestines, the instruments can be inserted through the rectum. Using a natural orifice like the mouth or the rectum can further reduce patient and hospital costs as anesthesia is generally not required. The elimination of anesthesia may also make such procedures less risky. Frequently, simply gaining access to the organ that is the subject of the surgery results in a substantial portion of the trauma to the patient during many medical procedures. Reducing this trauma in a safe and effective manner may make such procedures less costly and may make such procedures more widely available and more acceptable to the patient.

FIGS. 1-2 illustrate one prior art fastener used in NOTES procedures to join and anastomose tissue. The illustrated two part fastener is joined by coupling a first fastener part having a male portion with a second fastener part having a female portion. The male portion of the first fastener part may be operably configured to engage in a snap fit connection with the second fastener part. The first and second fastener parts may have laterally extending surfaces to increase the surface area of the fastener to improve tissue retention therebetween.

The fastener illustrated in FIGS. 1-2 may be suitable for retaining tissue therebetween, however, a clinician may be provided with a limited amount of assurance regarding the integrity of the coupling between the first and second fastener parts. Should the snap fit of the fastener fail, the joined tissue may separate resulting in a potentially life threatening complication. It would therefore be advantageous to provide a fastener operably configured to join tissue that provides an improved measure of assurance to a clinician regarding the integrity of the coupling.

BRIEF SUMMARY OF THE INVENTION

In the present invention, an anastomosis device for attaching two hollow organs together and creating a passage therebetween is provided. The anastomotic device includes a first tissue clamp member, a second tissue clamp member, and an adhesive for locking the first tissue clamp member and the second tissue clamp member together. The first tissue clamp member and the second tissue clamp member are locked in a spaced apart orientation to enable the clamping of tissue between the first tissue clamp member and the second tissue clamp member.

Also in accordance with the present invention, there is provided a method of creating a passage in tissue between a pair of hollow organs. First, the method includes a step of providing an anastomotic device for clamping on tissue. The anastomotic device includes a first tissue clamp member, a second tissue clamp member, and an adhesive in at least one of the first tissue clamp member and the second tissue clamp member. Second, a first hollow organ is aligned with a second hollow organ in a desired orientation. Third, the first tissue clamp member or the second tissue clamp member is placed into the first hollow organ. Then, the other of the first tissue clamp member or second tissue clamp member is placed in opposition into the second hollow organ. Fourth, the first tissue clamp member and the second tissue clamp members are clamped together in a spaced apart orientation to clamp tissue therebetween, and the first and second rings are locked together with the adhesive.

BRIEF DESCRIPTION OF THE FIGURES

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 11 is a more detailed partial cross sectional view of the fastener cassette of FIG. 9 showing the first fastener element recessed into the fastener cassette.

DETAILED DESCRIPTION OF THE INVENTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

Figure 3:
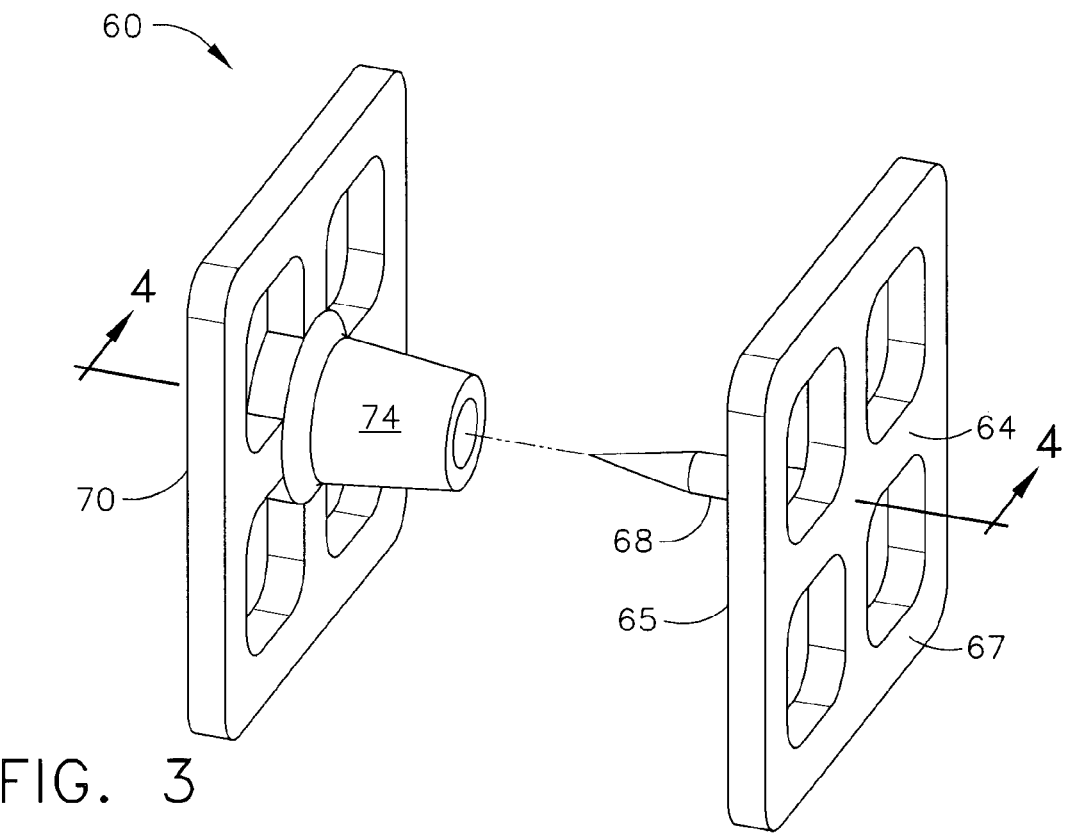
FIG. 3 is an isometric view of one version of a fastener having a first clamp member and a second clamp member shown spaced apart.

Turning to the Figures, wherein like numerals denote like components throughout the several views, FIG. 3 illustrates a two-piece anastomosis fastener 60 that can be used to in two organs or organ sections. The fastener 60 may be releasably attached to a fastener applying instrument, such as the fastener applying instrument 116, illustrated in FIG. 6. In the illustrated version, the fastener 60 includes a first member 65 and a second member 70, where the clamp members 65, 70 are operably configured to be fastened together with an adhesive to clamp and hold tissue, such as gastric tissue, in juxtaposition to establish an anastomosis. The first clamp member 65 and the second clamp member 70 lock together with an adhesive.

Figure 1:
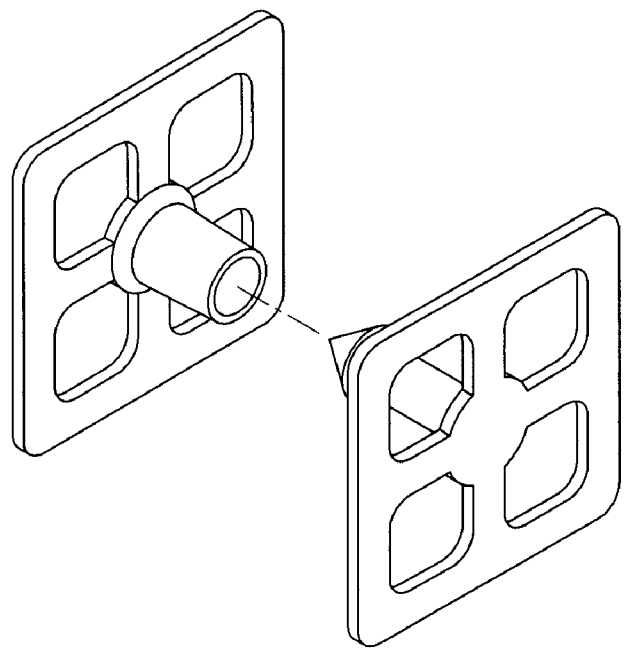
FIG. 1 is an exploded view of a prior art mechanical fastener having a first member and a second member.
Figure 2:
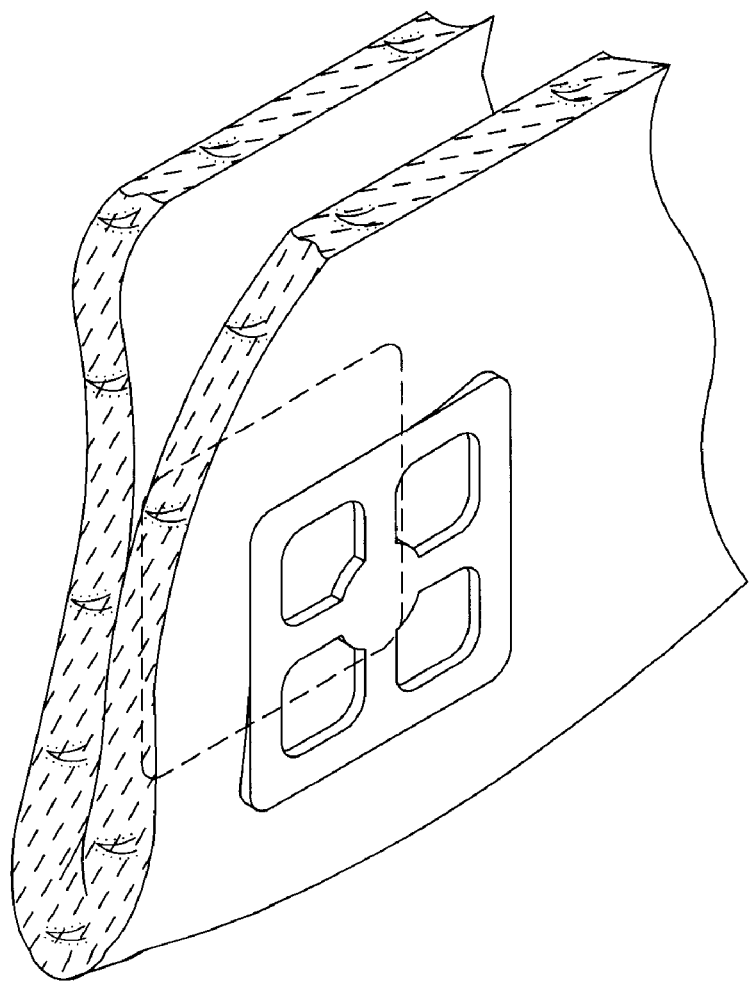
FIG. 2 is an isometric view of the prior art mechanical fastener of FIG. 1 shown with a fold of gastric tissue sandwiched between the first member and the second member.
Figure 4:
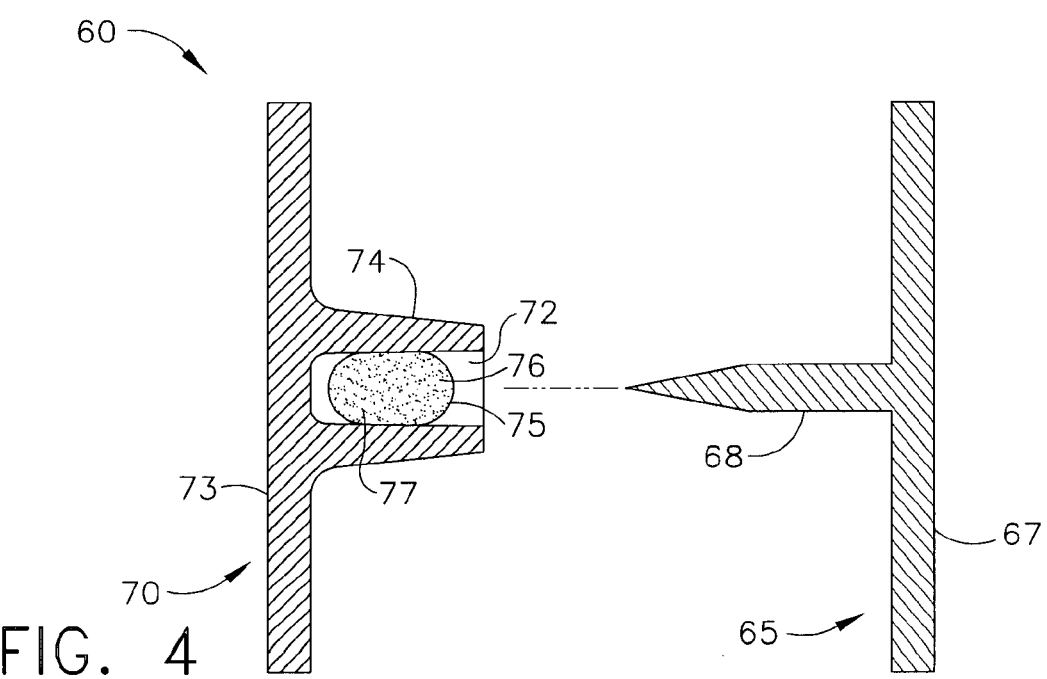
FIG. 4 is a cross-sectional view of the adhesive fastener of FIG. 7 taken along line 4-4 showing the first fastener and the second fastener member prior to engagement.

FIG. 4 is a cross-sectional view of the fastener 60 of FIG. 1, taken along line 2-2, shown with the first clamp member 65 and the second clamp member 70 separated and spaced apart. The first clamp member 65 includes a first flange 67 projecting laterally from a projection or point 68. The second clamp member 70 may have a second flange 73 projecting laterally from a socket 74. The two-piece anastomosis fastener 60 may be made from any suitable material including, but not limited to, metallic materials including stainless steel, gold, or titanium, and plastics including polyethylenes, polyetheretherketones (PEEK) and bioabsorbables such as polylactic acid (PLA), polyglycolic acid (PGA) and their copolymers. Alternately, the two-piece anastomosis fastener 60 may be made from a number of absorbable implantable materials such as, but not limited to, polylactic acid (PLA), polyglycolic acid (PGA) and their copolymers, and absorbable materials used for sutures such as dexon, vicryl, polydioxanone, and polyglyconate.

Still referring to FIG. 4, shown is a passageway 72 in the socket 74. A sealed container, bladder, or ampoule 75 may be fixably located in the passageway 72 of the socket 74 and may contain an adhesive 76. The adhesive 76 may be released from frangible ampoules 75 when penetrated or ruptured, such as by point 68, when the first clamp member 65 and the second clamp member 70 are joined. The adhesive 76 within the ampoules 75 may be sealed to provide stability, to increase shelf-life, and to prevent premature setting of the adhesive 76. The ampoules 75 may be made from any suitable material, or combination of materials, including, for example, coatings, glasses, plastic materials, metallic materials, gels, or ceramics. By way of example, plastic materials may include butyrate or polyethylene rubber, silicone or plastic material, such as, for example, polyvinyl chloride, polyethylene, polyurethane, natural or nitril rubber, or any combination thereof. Pierceable metal, such as aluminum or gold, may be used for the ampoule 75. An example of a suitable ampoule that can be used is disclosed in U.S. Pat. No. 5,928,611, the entire disclosure of which is incorporated herein by reference. In an alternate version, the ampoule 75 may include placing adhesive 76 into the bore of the socket 74 and inserting or applying a barrier material or plug (not shown) into the socket 74 over the adhesive 76 to act as a seal or airtight seal for adhesive 76. The plug may be configured from any suitable material, such as the materials listed with reference to the ampoule 76, or any other material that could act as a barrier.

By way of example, the adhesive 76 may be a single part or a dual part adhesive that is a polymerizable and/or a cross-linkable material such as a cyanoacrylate adhesive. The adhesive material may be a monomeric (including prepolymeric) adhesive composition, a, polymeric adhesive composition, or any other natural or artificial compound suitably configured to couple the first clamp member 65 and second clamp member 70 together when joined. In one version, the monomer is a 1,1-disubstituted ethylene monomer such as an alpha-cyanoacrylate. When cross linked, the cyanoacrylate changes from a liquid to a solid. A cross linked adhesive can be rigid or flexible, non-permeable or permeable. In one version, the point 68 of the first clamp member 65 may be doped with an initiator such that engagement of the point 68 with the adhesive 67 causes the adhesive 67 to solidify and bond the fastener 60. It will be appreciated that any suitable adhesive and initiator configuration is contemplated where, for example, the initiator may be incorporated directly into the material of a clamp member.

The adhesive 76 may be a single part or dual part adhesive that may contain one or more additives 77. Examples of suitable additives 77 include, but are not limited to, anesthetics, sclerotic agents, necrosing agents, plasticizing agents, thixotropic agents, buffers, catalysts, adhesive initiators, fillers, micro particles, thickeners, solvents, drugs, medicaments, natural or synthetic rubbers, stabilizers, pH modifiers, bioactive agents, cross-linking agents, chain transfer agents, fibrous reinforcements, colorants, preservatives, formaldehyde reducing agents, scavenging agents, flavorants, perfumes, combinations thereof, and the like. Other suitable single part and dual part adhesives 76 and additives 77 may be found in United States Application 2004/0190975 by Goodman et al. which is hereby incorporated by reference in its entirety.

In an alternate version, the ampoule 75 may contain a plurality of separate chambers where, for example, an adhesive 76 may be placed in one chamber and an additive 77 in the other. Dual chamber ampoules may also be used for two part adhesives which would mix, for example, when penetrated by the point 68. Multiple chambers may also be used to house polymerization initiators, drugs, medicaments, or any other suitable additive such as those disclosed herein. Alternately, instead of adhesive 76, the ampoule 75 may solely contain additives 77 such as adhesive initiators or compounds to induce the setting of externally applied adhesives. As will be discussed herein, a plurality of ampoules 75 containing adhesive 76 and/or additives 77 in any suitable relationship or configuration are contemplated. For example, where a plurality of ampoules 75 are provided, the adhesives 76 and additives 77 may be placed in any order in the sockets 74 and/or more than one ampoule 75 may be placed in a single socket 74.

Figure 5:
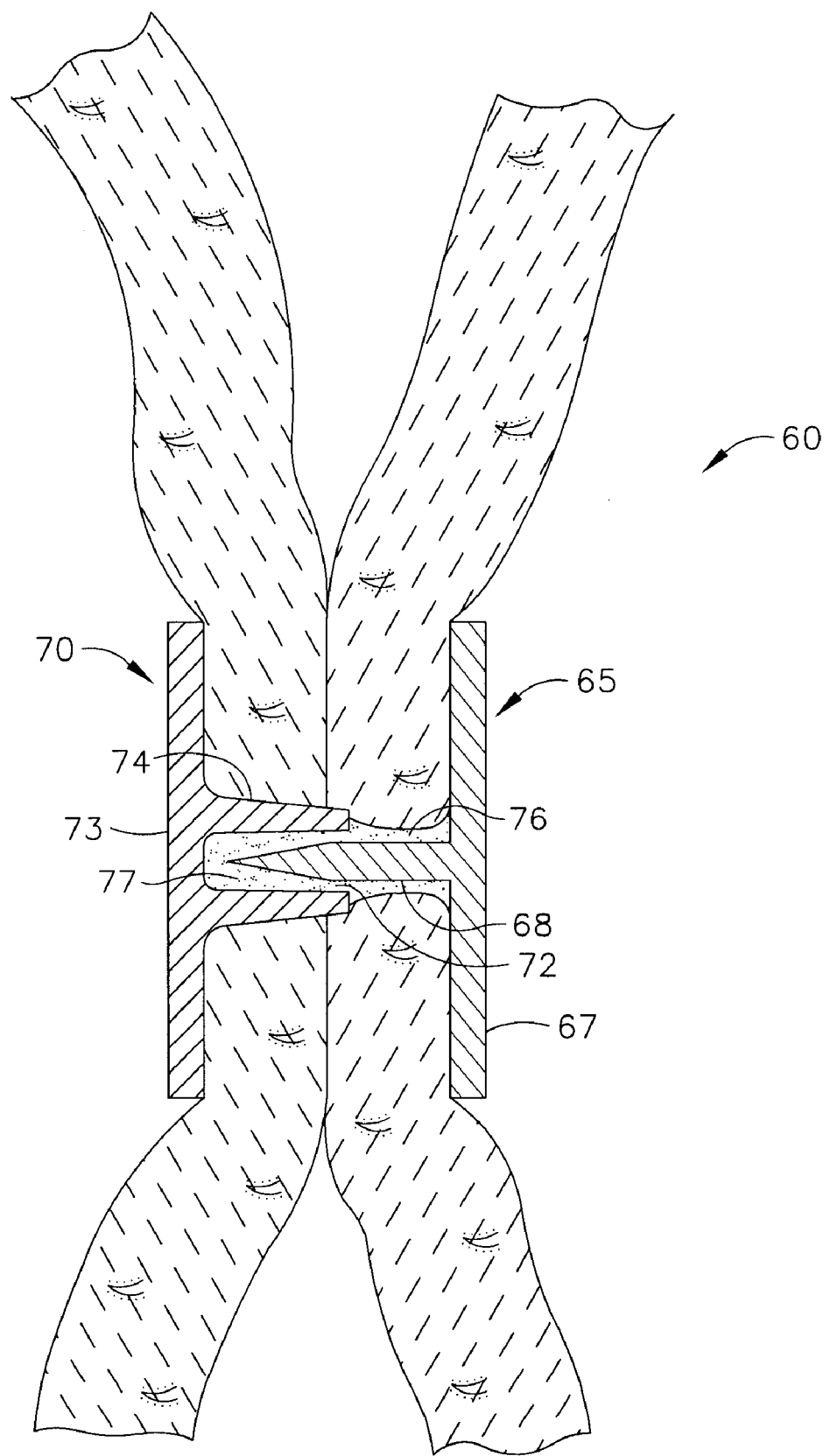
FIG. 5 is a cross-sectional view of the adhesive fastener of FIG. 7 taken along line 8-8 showing the first fastener engaged with the second fastener, where a fold of gastric tissue is shown sandwiched therebetween.

FIG. 5 shows the first clamp member 65 and the second clamp member 70 of the fastener 60 after being engaged with tissue retained therebetween. The first clamp member 65 and the second clamp member 70 may be joined by any suitable device or mechanism, such as the fastener delivery instrument 116 shown in FIG. 6, as will be discussed in further detail herein. In the illustrated version, coupling the fastener 60 includes urging the point 68 into the passageway 72 of the socket 74 and the point 68 into the ampoule 75, shown in FIG. 4, to release adhesive 76 and/or additive 77. Coupling the fastener in such a manner may permanently lock the first clamp member 65 and the second clamp member 70 together to secure tissue therebetween. In one version, the first member 65 and second member 70 are brought and held together to pinch, for example, gastric tissue therebetween. The pinching action may juxtapose the tissue such that an anastomosis is established. Clamping pressure from the first flange 67 and the second flange 73 may also ensure hemostasis and prevent bleeding. In the illustrated version, the adhesive 76 ensures that the first clamp member 65 and the second clamp member 70 are permanently locked together to prevent separation. The fastener 60 may include both adhesive and mechanical coupling. The fastener 60 may also be constructed from a bioabsorbable material, for example, such that the fastener 60 will temporarily maintain the coupling until sufficient healing has occurred.

Versions of the fastener 60 are disclosed by way of example only and could be adapted or modified for use in many other surgeries. For example, the length of spacers flanges 67, 73 may be lengthened or shortened to make a two piece fastener with adhesive 76 that could be used to attach two pieces of tissue, such as intestine, of a different thickness together. Alternately, a fastener with adhesive could be used to create an opening for the passage of feces from a patient with a colostomy and could incorporate features for the attachment of a colostomy bag.

In an alternate version, the first clamp member 65 and the second clamp member 70 are configured from a bioabsorbable material. Such a configuration may enable the fastener 60 to be used as a temporary connection to hold tissue in place until healing or an anastomosis has occurred, after which the fastener would break down and be absorbed. If desired, during the attachment of the fastener 60, a sheet adhesive comprising a solid film, a uniform carrier or a mesh-like carrier could be placed between tissue (not shown). The sheet adhesive could be any adhesive referenced above. When the first clamp member 65 and the second clamp member 70 are engaged, the sheet adhesive may be activated with moisture in the tissue or from an initiator additive 77 in an ampoule 75 associated with the second clamp member 70. It will be appreciated that multiple variations utilizing sheet adhesive in combination with an initiator, or vice versa, are contemplated.

Figure 6:
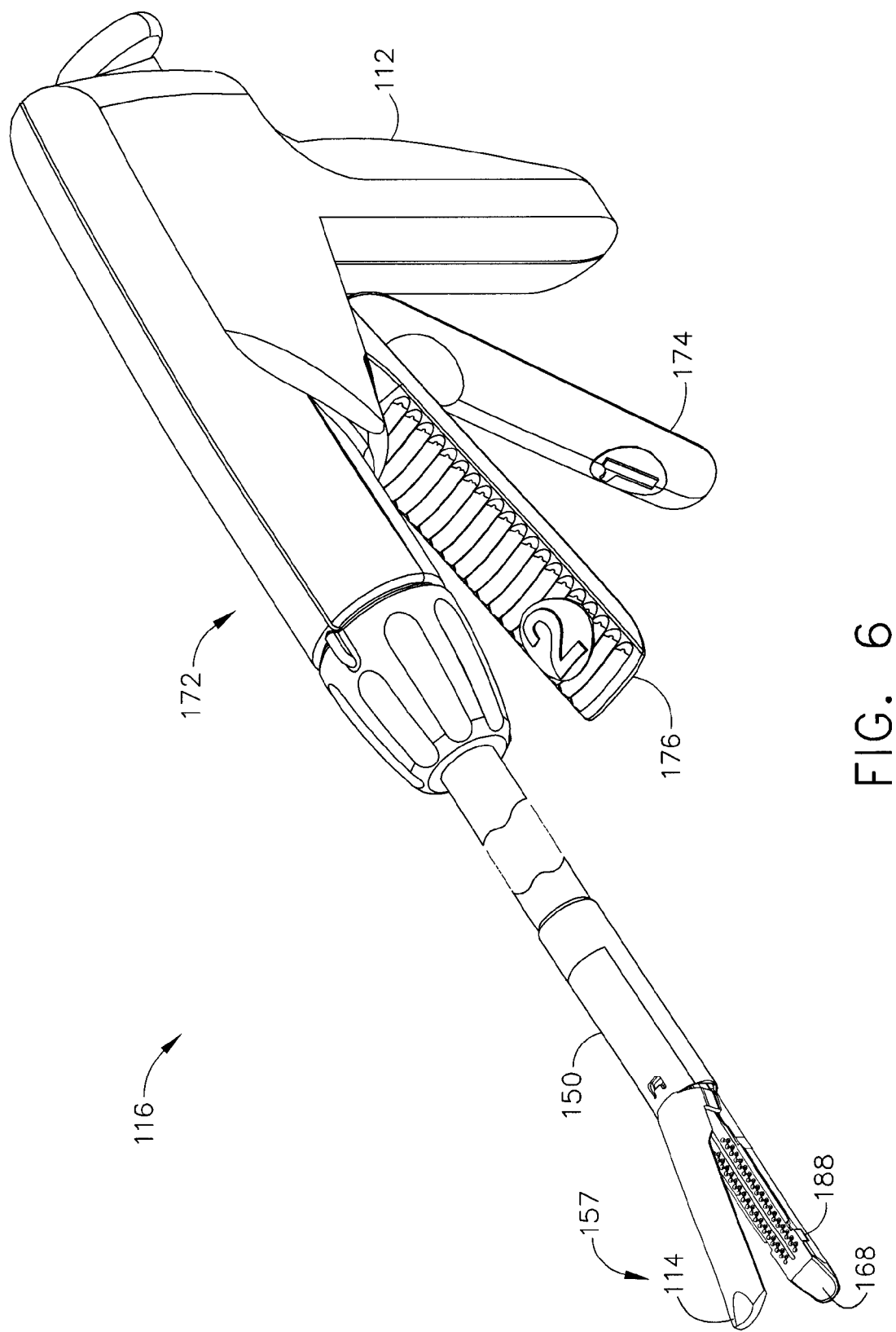
FIG. 6 is an isometric view of a surgical instrument having an end effector operably configured to deploy a two part fastener.

FIG. 6 is an isometric view of one version of a fastener applying instrument 116 including an end effector 157 and a handle 172. The fastener applying instrument may be any suitable delivery instrument commonly known in the art including, for example, the instruments disclosed in U.S. Pat. No. 5,951,552 to Long and U.S. Pat. No. 5,597,107 to Knodel, which are herein incorporated by reference in their entirety. The handle 172 includes a grip 162, a grasping trigger 174 and a firing trigger 176. In the illustrated version, pivotal movement of the grasping trigger 174 results, for example, in distal movement of a yoke (not shown) and a closure tube 150 thereby closing an anvil 114 against a fastener cartridge 168 which is positioned in a cartridge channel 188. In one version, pivotal movement of the grasping trigger 174 further releases a firing rod (not shown) and positions the firing trigger 176 to engage a drive member (not shown). In the illustrated version, further pivotal movement of the firing trigger 176 toward the grip 162 results in distal movement of the drive member which fires the fastener, such as the fastener 260 shown in FIG. 7, housed in fastener cartridge 168. It will be appreciated that any suitable delivery device or mechanism may be provided.

Figure 7:
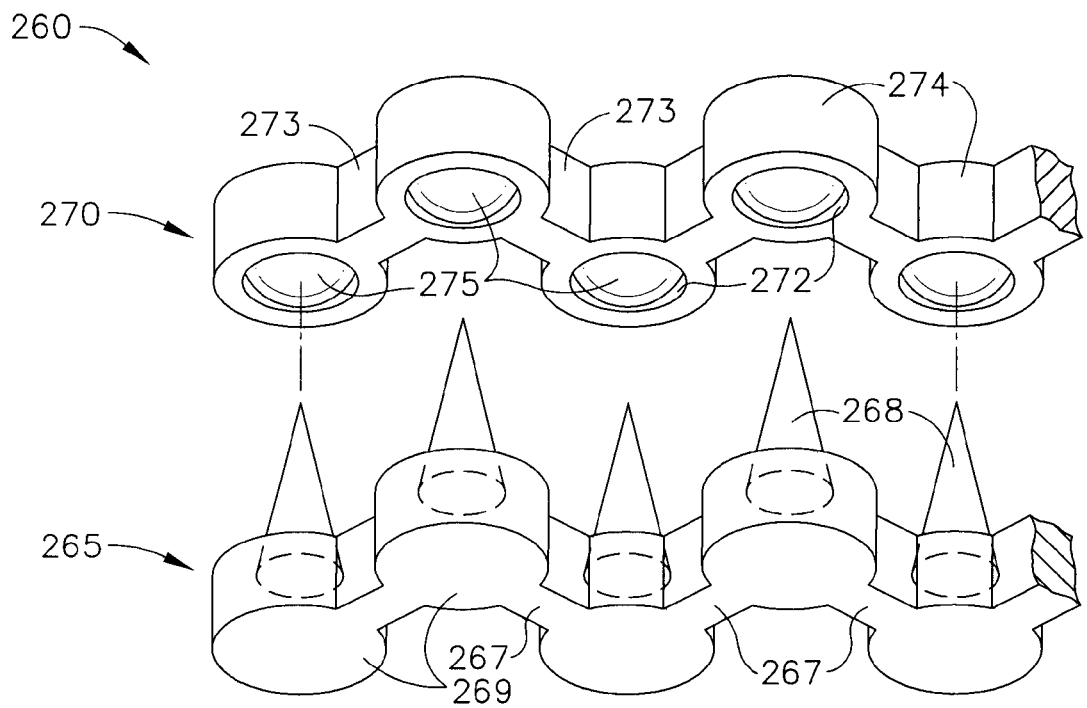
FIG. 7 is an exploded view of an alternate version of an adhesive fastener having a first fastener member and a second fastener member.

FIG. 7 is an alternate version of a two-piece anastomosis fastener 260 that can be used to join two organs or organ sections together. The fastener 260 may be releasably attached to a fastener applying instrument, such as the fastener applying instrument 116, illustrated in FIG. 6. In the illustrated version, the fastener 260 includes a first member 265 and a second member 270, where the clamp members 265, 270 are operably configured to fasten together to clamp and hold tissue, such as gastric tissue, in juxtaposition to establish an anastomosis. The first clamp member 265 and the second clamp member 270 lock together with an adhesive.

The fastener 260 is shown with the first clamp member 265 and the second clamp member 270 separated and spaced apart. The first clamp member 265 includes a plurality of connection members 267 projecting laterally from the bases 269 of a plurality of projections or points 268. The second clamp member 270 may have a plurality of connection members 273 projecting laterally from a plurality of sockets 274. The two-piece anastomosis fastener 260 may be made from any suitable materials including, but not limited to, metallic materials including stainless steel, gold, or titanium, and plastics including polyethylenes, polyetheretherketones (PEEK) and bioabsorbables such as polylactic acid (PLA), polyglycolic acid (PGA) and their copolymers. Alternately, the two-piece anastomosis fastener 260 may be made from a number of absorbable implantable materials such, as but not limited to, polylactic acid (PLA), polyglycolic acid (PGA) and their copolymers, and absorbable materials used for sutures such as dexon, vicryl, polydioxanone, and polyglyconate.

Still referring to FIG. 7, shown are passageways 272 in the sockets 274. A sealed container, bladder, or ampoules 275 may be fixably located in the passageways 272 of the sockets 274 and may contain an adhesive 276. The adhesive 276 may be released from the frangible ampoules 275 when penetrated or ruptured, such as by points 268, when the first clamp member 265 and the second clamp member 270 are joined. The adhesive 276 within the ampoules 275 may be sealed to provide stability, to increase shelf-life, and to prevent premature setting of the adhesive 276. The ampoules 275 may be made from any suitable material, or combination of materials, including, for example, coatings, glasses, plastic materials, metallic materials, gels, or ceramics. By way of example, plastic materials may include butyrate or polyethylene rubber, silicone or plastic material, such as, for example, polyvinyl chloride, polyethylene, polyurethane, natural or nitril rubber, or any combination thereof. Pierceable metal, such as aluminum or gold, may be used for the ampoule 275. In an alternate version, the ampoule 275 includes placing adhesive 276 into the passageways 272 of the sockets 274 and inserting or applying a barrier material or plug (not shown) into the sockets 274 over the adhesive 276 to act as a seal or airtight seal for adhesive 276. The plug may be configured from any suitable material, such as the materials listed with reference to the ampoule 275, or any other material that could act as a barrier.

Figure 8:
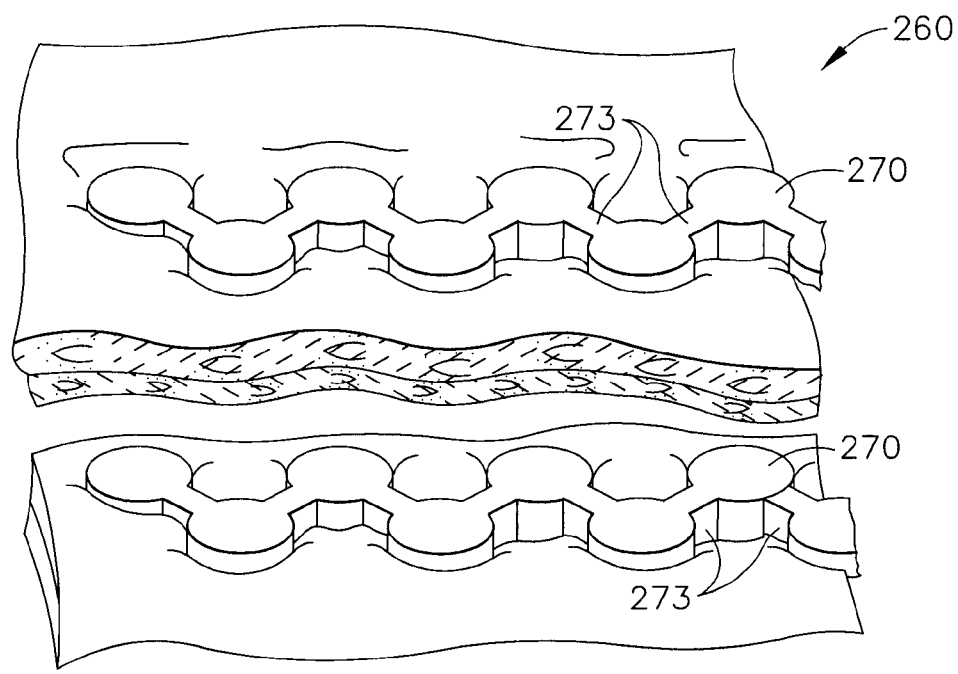
FIG. 8 is a partial isometric view of the adhesive fastener shown in FIG. 7 showing the adhesive fastener adhered together in tissue with the surgical instrument of FIG. 6 removed.

FIG. 8 shows one version of the fastener 260 after engagement with tissue retained therebetween. The first clamp member 265 and the second clamp member 270 may be joined by any suitable device or mechanism, such as the fastener delivery instrument 116 shown in FIG. 6. In the illustrated version, coupling the fastener 260 moves the points 268 into the passageways 272 of the sockets 274 and the points 268 into the ampoules 275, shown in FIG. 7, to release additive, adhesive, or the like. Coupling the fastener 260 in such a manner may permanently lock the first clamp member 265 and the second clamp member 270 together. In one version, the first clamp member 265 and second member 270 are brought and held together to pinch, for example, gastric tissue therebetween. The pinching action may juxtapose the tissue such that an anastomosis is established. In the illustrated version, the adhesive 76 ensures that the first clamp member 65 and the second clamp member 70 are permanently locked together to prevent separation. The fastener 60 may include both adhesive and mechanical coupling. The fastener 60 may be constructed from a bioabsorbable material, for example, such that the coupling of the fastener 60 is permanent until the fastener is substantially disintegrated and the anastomosis is formed.

The stepped configuration of the first clamp member 265 and the second clamp member 270 may simulate a suture line commonly used in NOTES procedures. As illustrated, the fastener 260 may include a plurality of points 268 and corresponding sockets 274, where the coupling therebetween may function as a line of sutures suitable for connecting tissue. The coupling of the points 268 and the sockets 274 may simulate sutures and the connection members 267, 273 may resemble the connections therebetween to provide compression, or the like. In such a manner, tissue portions may be joined with the fastener 260 for any suitable purpose in an efficient and minimally invasive manner. The fastener 260 may obviate the need for cumbersome hand suturing associated with creating an anastomosis during open surgery. The adhesive connection of the fastener 260 may help insure that the fastener 260 remains coupled and may provide clinicians with an additional measure of assurance that the coupling will not detach under pressure after completion of the procedure.

Figure 9:
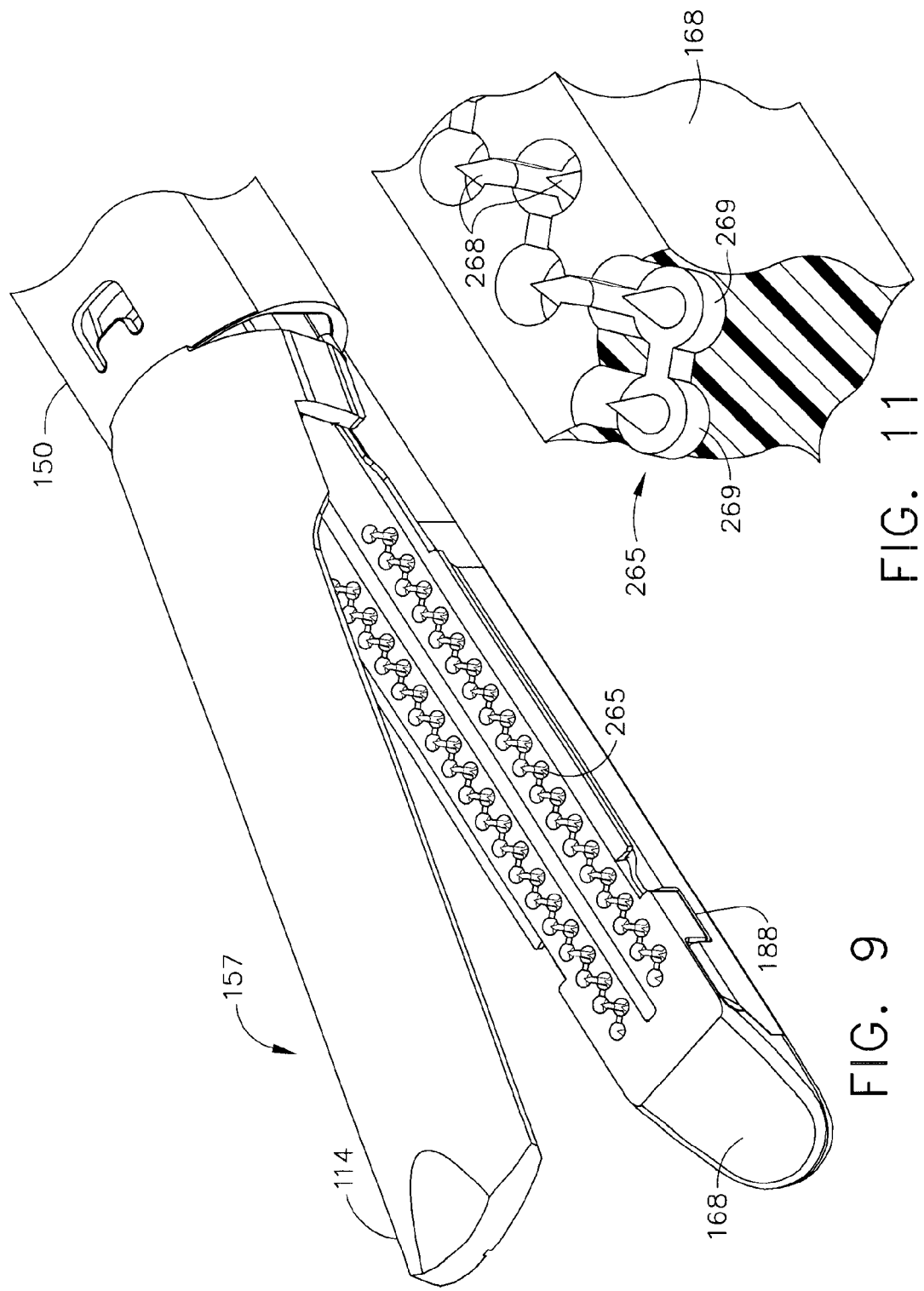
FIG. 9 is a more detailed top isometric view of the end effector of the surgical instrument of FIG. 6 showing an anvil and a fastener cassette in an open position, where the fastener cassette includes a first clamp member.
Figure 10:
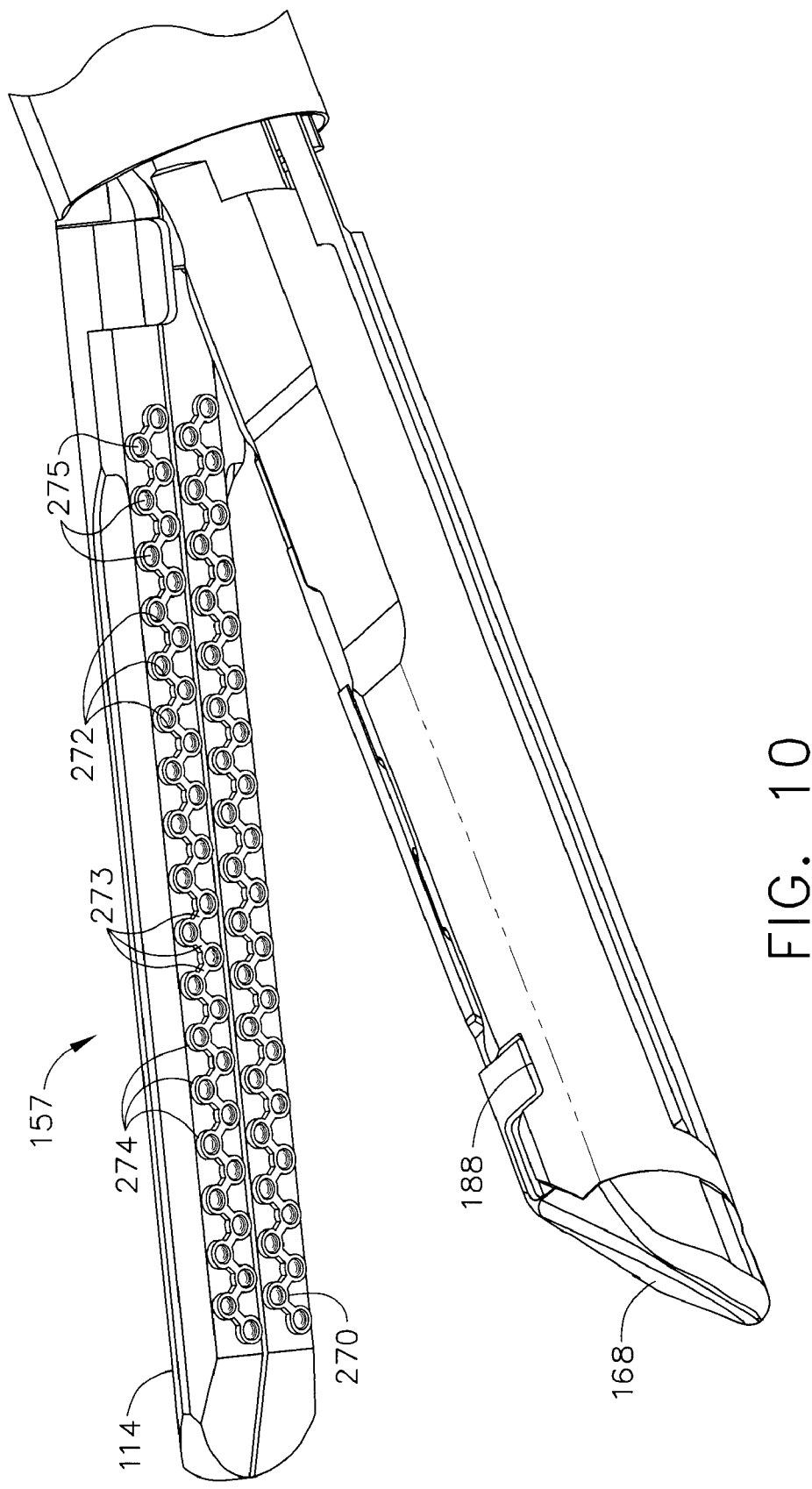
FIG. 10 is a more detailed bottom isometric view of the end effector of the surgical instrument of FIG. 6 showing a second clamp member associated with the anvil.

FIGS. 9-11 illustrate one device and method for retaining the fastener 260. In the illustrated version, a fastener delivery instrument 116 is provided for placement of the fastener 260 during, for example, a NOTES procedure. The fastener cartridge 168 is retained within the cartridge channel 188 of the end effector 157. The fastener 260 may be retained such that the first clamp member 265 is recessed into the fastener cassette 168. The first clamp member 265, having a plurality of points 268, may be recessed in a first state prior to delivery to prevent the points 268 from inadvertently catching and damaging tissue. Recessing, or otherwise guarding, the points 268 may prevent accidental tissue tears or punctures that could result in surgical complications.

In one version, after placement of tissue between the anvil 114 and the fastener cassette 168, pivotal movement of the grasping trigger 174 of the fastener delivery instrument 116, shown in FIG. 6, releases a firing rod and positions the firing trigger 176 to engage a drive member. Further pivotal movement of the firing trigger 176 toward the grip 162 results in distal movement of the drive member which fires the first clamp member 265 of the fastener 260. The first clamp member 265 may be fired toward the anvil 114 having the second clamp member 270, as illustrated in FIG. 10, associated therewith. The second clamp member 270 may be releasably coupled with the anvil 114 and may be configured such that it is substantially aligned with the first clamp member 265 of the fastener cassette 268. When the first clamp member 265 is fired, the points 268 associated therewith may penetrate the ampoules 265 retained within the passageways 272 of the sockets 274 to engage the first clamp member 265 and the second clamp member 270. The second clamp member 270 associated with the anvil 114 may remain static as the first clamp member 265 is actively engaged.

Once the first clamp member 265 is engaged with the second clamp member 270, as shown for example with reference to FIGS. 5 and 8, the ampoules 265 are punctured such that the adhesive 267 spreads and fills the space between and around the points 268 and the sockets 274. The adhesive 267 may surround the points 268 such that they become permanently coupled with the sockets 274. The depth of the passageways 272 and the length of the points 268 may be configured such that when engaged, a predetermined space between the connection members 267, 273 or flanges 67, 73 is reserved for tissue retention therebetween. As discussed with reference to other versions herein, the fastener may be a permanent fastener, a bioabsorbable fastener, an adhesive fastener, an adhesive and mechanical fastener, or may be provided with any other suitable configuration. It will be appreciated that various configurations of the fastener 260 are contemplated, including configurations having sockets 274 and points 268 of varying size and shape, such that various types and sizes of tissue may be accommodated. It will be further appreciated that any combination or configuration of adhesive and/or additive may be provided to achieve a desirable coupling effect.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

While the present invention has been illustrated by description of several embodiments and while the illustrative embodiments have been described in considerable detail, it is not the intention of the applicant to restrict or in any way limit the scope of the appended claims to such detail. Additional advantages and modifications may readily appear to those skilled in the art.

For example, whereas the surgical implant uses pinching to anastomose or bind tissue to facilitate healing or anastomosis, it is also within the scope of the invention to provide fasteners configured with drugs, anesthetics, sclerotic, and/or necrosing agents.

What is claimed is:

1. A surgical implant for clamping gastric tissue in a natural orifice transendoscopic surgical procedure comprising:
   a) a first tissue clamp member, wherein the first tissue clamp member comprises a plurality of sockets and a first plurality of connection members, wherein the sockets project laterally from the first plurality of connection members, wherein the first plurality of connection members together form a zig-zag configuration;
   b) a second tissue clamp member, wherein the second tissue clamp member comprises a plurality of projections and a second plurality of connection members, wherein the projections project laterally from the second plurality of connection members, wherein the sockets and the projections are sized and configured such that the projections are insertable into corresponding ones of the sockets, wherein the projections are further configured to penetrate tissue, wherein the second plurality of connection members together form a zig-zag configuration complementing the zig-zag configuration of the first plurality of connection members, wherein both of the first and second tissue clamp members are configured to engage together as the first and second tissue clamp members are adjusted to a spaced apart orientation with tissue clamped therebetween; and c) an adhesive for locking the first and the second tissue clamp members together in the spaced apart orientation to clamp tissue between the first and the second tissue clamp members, wherein at least a portion of the adhesive is positioned in the plurality of sockets.

2. The surgical implant of claim 1, wherein the adhesive is compound selected from the group consisting of a polymerizable monomer, a polymerizable 1,1, 1,1-disubstituted ethylene monomer, a cyanoacrylate formulation, and combinations thereof.

3. The surgical implant of claim 1, wherein the first tissue clamp member includes a first flange member and the second tissue clamp member includes a second flange member operably configured to retain tissue therebetween.

4. The surgical implant of claim 1, wherein an additive is contained in at least one of the first clamp member and the second clamp member.

5. The surgical implant of claim 1, wherein the adhesive is encapsulated in an ampoule.

6. The surgical implant of claim 5, wherein the adhesive is selected from the group consisting of a single part adhesive, a two part adhesive, an additive, and combinations thereof.

7. The surgical implant of claim 5, wherein the adhesive further comprises one or more additives selected from the group consisting of anesthesia agents, sclerotic agents, necrosing agents, drugs, medicaments, adhesion initiators, micro particles, bioactive agents, and combinations thereof.

8. The surgical implant of claim 5, wherein at least one of the projections is operably configured to pierce the ampoule such that the contents thereof are released.

9. The surgical implant of claim 5, wherein the first tissue clamp member and the second tissue clamp member are constructed from a material selected from the group consisting of stainless steel, gold, titanium, polyethylene polymers, polyetheretherketones, polylactic acid, polyglycolic acid, polyglactin, polydioxanone, polyglyconate, and combinations thereof.

* * * * *